US011617717B2

(12) United States Patent
Lin et al.

(10) Patent No.: US 11,617,717 B2
(45) Date of Patent: *Apr. 4, 2023

(54) ANTI-INFECTION AND ANTI-TUMOR MUCOSAL IMMUNE PREPARATION

(71) Applicants: Haixiang Lin, Beijing (CN); Fang Liu, Beijing (CN); Li Zha, Beijing (CN); Xiaolin Sun, Beijing (CN)

(72) Inventors: Haixiang Lin, Beijing (CN); Fang Liu, Beijing (CN); Li Zha, Beijing (CN); Xiaolin Sun, Beijing (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/011,619

(22) Filed: Jun. 18, 2018

(65) Prior Publication Data

US 2018/0360738 A1  Dec. 20, 2018

(30) Foreign Application Priority Data

Jun. 19, 2017 (CN) .......................... 201710466207.1

(51) Int. Cl.
```
A61K 47/36        (2006.01)
A61K 39/39        (2006.01)
A61K 39/00        (2006.01)
A61K 9/00         (2006.01)
A61K 39/145       (2006.01)
A61K 47/34        (2017.01)
```

(52) U.S. Cl.
CPC ............ *A61K 9/008* (2013.01); *A61K 9/0043* (2013.01); *A61K 9/0073* (2013.01); *A61K 39/145* (2013.01); *A61K 39/39* (2013.01); *A61K 47/34* (2013.01); *A61K 47/36* (2013.01); *A61K 2039/541* (2013.01); *A61K 2039/543* (2013.01); *A61K 2039/544* (2013.01); *A61K 2039/60* (2013.01); *A61K 2039/6087* (2013.01); *A61K 2039/6093* (2013.01)

(58) Field of Classification Search
None
See application file for complete search history.

(56) References Cited

U.S. PATENT DOCUMENTS

| | | | | | |
|---|---|---|---|---|---|
| 5,532,159 | A | * | 7/1996 | Webb | A61P 35/00 435/344.1 |
| 7,838,017 | B2 | * | 11/2010 | Haixiang | A61K 9/2009 424/278.1 |
| 8,303,965 | B2 | * | 11/2012 | Lin | A61K 9/2009 424/278.1 |
| 8,303,966 | B2 | * | 11/2012 | Lin | A61K 33/00 424/278.1 |
| 2007/0166239 | A1 | * | 7/2007 | Lin | A61K 39/00 424/46 |
| 2008/0095810 | A1 | * | 4/2008 | Alonso Fernandez | A61K 9/5161 424/401 |
| 2009/0175902 | A1 | | 7/2009 | Lin | |
| 2011/0118200 | A1 | * | 5/2011 | Hu | C08B 37/003 514/34 |

FOREIGN PATENT DOCUMENTS

| | | | |
|---|---|---|---|
| CN | 105396130 A | * | 3/2016 |
| CN | 105396130 A | | 3/2016 |
| CN | 105555308 A | | 5/2016 |
| CN | 106075432 A | | 11/2016 |

OTHER PUBLICATIONS

Lin machine translation, Mar. 16, 2016.*

* cited by examiner

*Primary Examiner* — Robert T. Crow
*Assistant Examiner* — John P Nguyen

(57) ABSTRACT

The present invention relates to an anti-infection and anti-tumor mucosal immune preparation. The mucosal immune preparation includes mucosal immune substances that are mainly formed by organically bonding polyinosinic-polycytidylic acid, non-antibiotic amino compounds and metal cations through chemical bonds. The present invention provides a slow release effect on a local part or the whole body, prevents the degradation of serum ribonucleases of human beings and primates, prolong the half-life period of the mucosal immune preparation, increases the availability and effectiveness of drugs. The mucosal immune preparation can facilitate the mucosal immunity of the body by mucosal immunity and thus facilitate the activation and proliferation of various immune cells, rather than merely acting on diseased local parts, so that the purposes of anti-infection and anti-tumor prevention and treatment with almost no side effects are realized. Mucosal immunity also avoids the pain of repeated injection so that good compliance is achieved.

11 Claims, No Drawings

ANTI-INFECTION AND ANTI-TUMOR MUCOSAL IMMUNE PREPARATION

TECHNICAL FIELD

The present invention relates to the field of immunology, and in particular to an anti-infection and anti-tumor mucosal immune preparation.

BACKGROUND OF THE INVENTION

Anti-tumor and anti-virus therapies are major challenges at present. Three anti-tumor therapies (i.e., operative therapy, radiotherapy and chemotherapy) and immunotherapies such as PD1/PD-L1 or CTLA4 are targeted at treatment of local parts of or the local environment of tumors, with poor effects on metastatic cancers. Existing anti-virus vaccines are preventative and cannot be used for treatment.

The mucosal immune system is widely distributed in mucosal tissues of the respiratory system, the digestive system and the urogenital system and also in some exocrine glands, and is a main place for local or systemic immune responses.

Usually, the induction by injection immunity mainly works on humoral immunity. Various types of antibodies such as IgG antibodies are produced to neutralize pathogens after the pathogens enter the bodies. However, the injection immunity cannot induce effective local mucosal immune responses. Consequently, pathogens that cause infections by the mucosa cannot be blocked early by the injection-induced systemic humoral immunity, and the systemic immunity (humoral immunity and cellular immunity) can attack the pathogens only after the pathogens enter the bodies. However, when an adjuvant can promote the systemic immune responses, it is unable to determine that this adjuvant can certainly promote the mucosal immune responses. For example, after the aluminum hydroxide adjuvant is bonded with an antigen, the mucosal immune responses cannot be effectively promoted in the case of mucosal administration. On the other hand, the injection immunity is likely to cause the rupture of some capillaries in the muscle and skin at the injection site, resulting in subcutaneous bleeding. In the case of intramuscular injection, if the dosage is too large, the injection is too fast or the injection in a same site lasts for a long period of time, the induration will be caused since the drug liquid cannot be immediately absorbed. If the intramuscular injection into the buttocks is carried out for many times or the intramuscular injection into the buttocks is still carried out in a site where the induration or infection has already been found, it is likely to cause gluteus contracture and thus claudication.

As an analogue of the artificially-synthesized mimivirus dsRNA and a ligand fors of TLR3, RIG-I and MDA5, polyinosinic-polycytidylic acid can induce high-titer IFN-a in mice or cell cultures. However, the polyinosinic-polycytidylic acid has poor induction effect in human bodies and monkey bodies since there are nucleases that degrade the polyinosinic-polycytidylic acid in the blood of primates. Therefore, in the prior art, there have been many approaches of improving the deficiencies of the polyinosinic-polycytidylic acid.

CN105396130A disclosed a novel vaccine adjuvant and a vaccine containing the same, i.e., a polyinosinic-polycytidylic acid (PIC), ammonia and calcium adjuvant (a PIC-non-antibiotic amino compounds-calcium chloride adjuvant) and a vaccine containing the PIC, ammonia and calcium adjuvant. Kanamycin commonly used in the prior art is replaced with non-antibiotic amino compounds. The polyinosinic-polycytidylic acid as the main ingredient is easily degraded by nucleases in the body. Due to the hemodilution and the adhesion to mucous proteins in the injection administration, effective ingredients into a target organ have been consumed greatly.

SUMMARY OF THE INVENTION

In order to solve the problems in the prior art, an objective of the present invention is to provide an anti-infection and anti-tumor mucosal immune preparation.

For this purpose, the present invention employs the following technical solutions.

In a first aspect, the present invention provides an anti-infection and anti-tumor mucosal immune preparation, wherein the dosage form of the preparation is spray or aerosol; and, effective ingredients of the preparation include mucosal immune substances that are mainly formed by organically bonding polyinosinic-polycytidylic acid, non-antibiotic amino compounds and metal cations through chemical bonds.

Preferably, unlike the common spray or aerosol in the prior art, the preparation of the present invention contains neither adjuvants used in the common spray nor adjuvants and propellants used in the common aerosol.

The propellant is an ejection power source for the aerosol, and can also be used as a solvent or thinner for drugs. The propellant is mostly a liquefied gas that has an atmospheric boiling point lower than the room temperature and a high vapor pressure. When a valve is opened, the pressure drops suddenly, and the propellant is gasified rapidly, so that the drug in the container is sprayed out under the pressure of the propellant. Ideally, the vapor pressure of the propellant at the normal temperature should be greater than the atmospheric pressure; the propellant should be non-toxic and free of sensitization response and irritation; the propellant should be colorless, odorless and tasteless; the propellant should be stable in property, non-flammable and non-explosive, and should not interact with the drug or the container; and, the propellant should be cheap and readily available. As a constituent of the aerosol, sometimes, the propellant can be used as a solvent or thinner for the main drug. The property and dosage of the propellant are related to the particle size, humidity and the like of the aerosol. The propellant can be a compressed gas, for example, nitrogen, carbon dioxide or nitrous oxide. However, at present, the propellant in most cases is a liquefied gas having a boiling point lower than the room temperature, for example chloroalkanes such as trichlorofluoromethane, difluoromethane and trichlorotetrafluoroethane.

Further, preferably, the effective ingredients of the preparation are mucosal immune substances that are formed by organically bonding polyinosinic-polycytidylic acid (PIC), non-antibiotic amino compounds, metal cations and PEG and/or PEI and/or PLGA through chemical bonds The non-antibiotic amino compounds may be one or more selected from the following ingredients: glucosamine, chitosan oligosaccharide (COS), polyethyleneimine (PEI), graft of polyethylene glycol and chitosan oligosaccharide (PEG-g-COS), PEG-g-CS, graft of folic acid and chitosan oligosaccharide (FA-g-COS), graft of galactose, PEG and PEI (GAL-g-PEG-g-PEI), COS-g-PEG-g-PEI, CS-g-PEG-g-PEI, PEI-g-PEG, PEI-g-Cos, PEI-g-CS and the like.

The grafts involved in the non-antibiotic amino compounds may be prepared by the technical means known to those skilled in the art, for example, with reference to the following literatures: SUN Yiyi, HOU Shixiang, CHEN Tong, HE Jun, YUAN Ziyuan. 2005. Synthesis and Representation of Chitosan-Polyethylene Glycol Grafted Copolymer, *Journal of Sichuan University*, 37(2):76-79.; LIU Shi, XU Zhe, LUO Zhi, XIANG Guangya. 2006. Synthesis of Lactose Grafted Polyethylenimine Chitosan. *China Medical Herald*, 24(4):607-609.; and, ZHANG Xuan, PAN Shirong, LV Peng, HU Haimei, ZHANG Wei. 2006. Preparation and Representation of Polyethylene Glycol-Polyethylenimine Copolymer. *Journal of Sun Yatsen University*, 45(6):53-57. In the present invention, the non-antibiotic amino compounds are used as raw materials for preparing the mucosal immune preparation, and the method for preparing the non-antibiotic amino compounds is not limited.

In addition to the stable double-stranded polyinosinic-polycytidylic acid structure, the non-antibiotic amino compounds (e.g., chitosan oligosaccharide, etc.) used in the present invention further have a certain biological characteristic and activity. By compounding chitosan oligosaccharide or ligands for TLR4 with the polyinosinic-polycytidylic acid, the mucosal immune function is further enhanced.

The metal cations include but are not limited to $Ca^{2+}$, $Mg^{2+}$, $Zn^{2+}$, iron ions, lithium ions and the like, preferably, $Ca^{2+}$.

The above ingredients are organically bonded through chemical bonds such as hydrogen bonds, ionic bonds, covalent bonds or metallic bonds, and the resulting product is not a mixture.

Further, the non-antibiotic amino compounds are preferably chitosan oligosaccharide having a molecular weight of less than 3200 and glucosamine.

As a specific implementation of the present invention, a method for preparing the mucosal immune preparation includes the following steps.

Solution 1:

(1) A polyinosinic acid solution and a polycytidylic acid solution are prepared from polyinosinic acid and polycytidylic acid as raw materials by a PBS buffer solution, and the polyinosinic acid solution and the polycytidylic acid solution are stirred at 30° C. to 60° C. to obtain 0.5 mg/mL to 10 mg/mL of a double-stranded polyinosinic-polycytidylic acid solution (PIC solution).

(2) A chitosan oligosaccharide solution (COS solution) having a concentration of 1.6 mg/mL to 12.8 mg/mL is prepared from chitosan oligosaccharide by the PBS buffer solution.

(3) The COS solution is added dropwise in the double-stranded polyinosinic-polycytidylic acid solution obtained in the step (1) while stirring, a PEI solution is then added dropwise while stirring, and a $CaCl_2$) solution is added dropwise while stirring, to obtain a mucosal immune substance sample solution.

(4) The prepared mucosal immune substance sample solution is sterilized, filtered, and packaged in a proper spray bottle or aerosol bottle to obtain the product.

Or, solution 2:

(1) A polyinosinic acid solution and a polycytidylic acid solution are prepared from polyinosinic acid and polycytidylic acid as raw materials by a PBS buffer solution, and the polyinosinic acid solution and the polycytidylic acid solution are stirred at 30° C. to 60° C. to obtain 0.5 mg/mL to 10 mg/mL of a double-stranded polyinosinic-polycytidylic acid solution (PIC solution).

(2) A chitosan oligosaccharide solution (COS solution) having a concentration of 1.6 mg/mL to 12.8 mg/mL is prepared from chitosan oligosaccharide by using the PBS buffer solution.

Or, a PEG-g-COS solution having a concentration of 1.6 mg/mL to 51.2 mg/mL is prepared from PEG-g-COS by the PBS buffer solution.

(3) The PEG-g-COS solution or the COS solution is added dropwise in the double-stranded polyinosinic-polycytidylic acid solution obtained in the step (1) while stirring, and a $CaCl_2$) solution is then added dropwise while stirring to obtain a PIC-PEG-g-COS-$CaCl_2$) or PIC-COS-$CaCl_2$) compound.

(4) The PIC-PEG-g-COS-$CaCl_2$) or PIC-COS-$CaCl_2$) compound is stirred at a constant speed in a thermostatic magnetic stirrer and then added dropwise with 0.4 mg/mL to 6.0 mg/mL of an aqueous solution of sodium tripolyphosphate (TPP) until obvious opalescence is observed, the reaction is maintained for 10 min to 60 min to obtain a mucosal immune substance through ionic crosslinking and self-assembly, and the mucosal immune substance is centrifuged at a high speed to obtain a mucosal immune substance having a particle size of less than 1000 nm.

(5) The prepared mucosal immune substance is re-suspended by distilled water, sterilized, filtered, and packaged in a proper spray bottle or aerosol bottle to obtain the product.

Further, the effective ingredients of the preparation of the present invention include mucosal immune substances that are mainly formed by organically bonding polyinosinic-polycytidylic acid, non-antibiotic amino compounds, metal cations and PEG and/or PEI and/or PLGA and/or cationic polymers through chemical bonds. The cationic polymers are, for example, DEAE-glucosan, lipidosome and the like.

Further, the effective ingredients of the preparation of the present invention may further include mucosal immune substances that are mainly prepared from polyinosinic-polycytidylic acid, non-antibiotic amino compounds, metal cations and at least one of sodium tripolyphosphate (TPP), sodium alginate, borophenylic acid and catechol.

The preparation of the present invention further contains ligands for bonded RLRs and/or ligands for bonded CLRs and/or ligands for bonded NLRs and/or ligands for bonded TLRs and/or bonded immunomodulators, and at least one antigen and/or chemical drug and/or biological immune drug.

The ligands for bonded TLRs include: for example, peptidoglycan, biglycan, mannan, lipopeptid, glycolipid, atypical lipopolysaccharide, serum amyloid protein, CPG DNA, dsRNA, ssRNA, LPS, PGN, saturated fatty acid, lipoteichoic acid, resistin, lactoferrin, surfactant protein, trans-flagellin, hyaluronic acid, RNA-related antigen, Profilin-like molecules, etc.

The ligands for bonded RLRs include: for example, RNA, PIC, PICLC, PIC12u, etc.

The ligands for bonded CLRs include: for example, mannose and β-glucan on the surfaces of walls of fungal cells, etc.

The ligands for bonded NLRs include: for example, MDP, Mesθ DAP, etc.

The bonded immunomodulators include: cell factors (interleukin, interferon, tumor necrosis factors, colony stimulating factors, chemotactic factors and growth factors), mineral salts, aerosol cleaners, emulsifiers, saponifiers, particle releasers, chemotactic factors, activated ligands, dendritic cell costimulatory molecules, bacterial exotoxin, blocking antibodies, and T-cell activation preparations.

The bonded other chemical drugs include: (1) alkylating agents: cyclophosphamide, busulfan, dacarbazine, cisplatin, mustargen, melphalan, nitrosoureas, and derivatives thereof; (2) antimetabolites: 5-fluorouracil, methotrexate, cytarabine, ancitabine, hydroxyurea, and derivatives thereof; (3) antitumor antibiotics: actinomycin, mitomycin, biliflavin, adriamycin, daunomycin, dactinomycin, bleomycin, and derivatives thereof; (4) plant anticancer drugs: vinblastines, podophyllotoxins, harringtonines, maytansine, elemene emulsion, and derivatives thereof; (5) hormones: sex hormone, corticosteroid hormone, and derivatives thereof; and, (6) miscellaneous drugs: L-asparaginase, platinum compounds (cisplatin, carboplatin and oxaliplatin), dacarbazine, altretamine, and derivatives thereof.

The bonded other biological immune therapy drugs include: (1) immunocyte therapy drugs: TIL, DC, CIK, DC-CIK, NK, γδT cells, CD3AK, CAR-T, TCR-T, etc.; and, (2) antibody therapy drugs: anti-PD1 antibodies, anti-PDL1 antibodies, anti-CTLA4 antibodies, antibodies for resisting multiple kinds of CDs, etc.

Various bonded antigens, vaccines and bacterins include: bonded tumor antigens and vaccines, for example, one kind of tumor antigens among tumor-specific antigens, tumor-bonded antigens, tumor whole-cell antigens, tumor vesicles, dendritic cells-carried antigens and tumor polypeptides; bonded viral antigens and vaccines; and, bonded parasitic antigens and vaccines, as well as various antibodies prepared from diagnostic antigens.

The bonded tumor antigens are one kind of tumor antigens among bones, bone joints, muscles, lung, trachea, pharynx, nose, heart, spleen, arteries, veins, blood, blood capillaries, lymphonodus, lymphatic vessels, lymphatic liquid, oral cavity, pharynx, oesophagus, stomach, duodenum, small intestines, colon, anus, epityphlon, liver, gallbladder, pancreas, parotid gland, sublingual gland, urinary kidney, ureter, bladder, urethra, ovary, fallopian tube, uterus, vagina, genitals, scrotum, testis, seminiferous duct, penis, eyes, ears, nose, tongue, skin, brain, brainstem, medulla oblongata, marrow, cerebrospinal fluid, nerves, thyroid gland, parathyroid gland, adrenal gland, pituitary gland, pineal gland, pancreas islet, thymus gland, gonad, sublingual gland, parotid gland, tumor-specific antigens, tumor-bonded antigens, tumor whole-cell antigens, tumor vesicles, dendritic cells-carried antigens and tumor polypeptides.

The bonded viral antigens are one kind of viral antigens among DNA virus, RNA virus, protein virus (e.g., prion), euvirus and subvirus (including viroid, virusoid and prion), bacteriophage (bacteriovirus), plant virus (e.g., tobacco mosaic virus), aminal virus (e.g., avian influenza virus and smallpox virus), moderate virus (e.g., HIV), virulent virus (e.g., rabies virus) and viral peptides.

The bonded bacterial antigens are one kind of bacterial antigens among *staphylococcus, streptococcus, listeria, erysipelothrix, renibacterium, bacillus, fusobacterium, mycobacterium, actinomyces, nocardia, corynebacterium, rhodococcus, bacillus anthraci, erysipelas bacillus, Clostridium tetani, Listeria monocytogenes, Clostridium perfringens, bacillus chauvael, Mycobacterium tuberculosis, Escherichia coli, proteusbacillus vulgaris, Shigella dysenteriae, pneumobacillus, bacterium burgeri, Clostridium perfringens, haemophilus influenza, haemophilus parainfluenzae, Moraxella catarrhalis, acinetobacter, yersinia, Legionella pneumophila, Bordetella pertussis, bordetella parapertussia, shigella, pasteurella, Vibrio cholera, bacillus parahaemolyticus*, and bacterial peptides.

The bonded parasitic antigens are one kind of parasitic antigens among parasites (e.g., roundworm, hookworm, tapeworm, *entamoeba histolytica, giardia lamblia*, etc.) in the digestive duct, intraluminal parasites (e.g., *Trichomonas vaginalis*), intrahepatic parasites (e.g., liver fluke and hydatid cyst), intrapulmonary parasites (e.g., *paragonimus westermani*), brain tissue parasites (e.g., *cysticercus cellulosae* and *Toxoplasma gondii*), intravascular parasites (e.g., *schistosome*), lymphangial parasites (e.g., *filaria*), muscular tissue parasites (e.g., *trichinella larvae*), intracellular parasites (e.g., *plasmodium* and *leishmania*), bone tissue parasites (e.g., hydatid), dermatozoon (e.g., sarcoptic mite and follicle mite), intraocular parasites (e.g., *thelazia callipaeda* and *cysticercus cellulosae*) and parasitic polypeptides.

The substances for promoting mucosal immune absorption or mucosal adhesion include: surfactants: anionic surfactants (e.g., carboxylates, sulfonates, sulfates, phosphates, etc.), cationic surfactants (e.g., amine salts, quaternary ammonium salts, heterocyclic rings, onium salts, etc.), zwitterionic surfactants (e.g., carboxylates, sulfonates, phosphates, betaine, imidazoline, amino acids, etc.), nonionic surfactants (e.g., alkyl polyglucosides, polyoxyethylene, polyols, alkanolamides and block copolyethers), and special surfactants (e.g., fluorine-containing surfactants, silicon-containing surfactants, boron-containing surfactants, high-molecular surfactants, etc.); The chelating agents include: for example, polyphosphates, aminocarboxylic acid, 1,3-diketone, hydroxycarboxylic acid, polyamine, etc. The bonding agents include: water-soluble bonding agents (e.g., starch, dextrin, polyvinyl alcohol, carboxymethylcellulose, etc.), hot-melt bonding agents (e.g., polyurethane, polystyrene, polyacrylate, ethylene-vinyl acetate copolymer, etc.), solvent based bonding agents (e.g., shellac, butyl rubber, etc.), emulsion-type bonding agents (e.g., vinyl acetate resin, acrylic resin, chlorinated rubber, etc.), solvent-free liquid bonding agents (e.g., epoxy resin, etc.); and, The other substances include: for example, PLGA, dextran, polysaccharide, lipidosome, etc.

A method for preparing the preparation bonded with polypeptide or protein antigen musical immune substances is as follows.

Solution 1: The polypeptides or protein antigens are added during the formation of the musical immune substances: the ingredients are added in PEG-g-COS or COS matrix, and the polypeptides or protein antigens are bonded in an aqueous phase containing sodium tripolyphosphate (TPP). The ingredients need to be added in a proper ratio and stirred by magnetic beads at certain PH to form the musical immune substances. For example, the bonding ratio of the polypeptides or protein antigens to the musical immune substances is 1-100:1-100, and the pH during stirring and bonding is 3 to 8.

Solution 2: The polypeptides or protein antigens and the preformed musical immune substances are incubated so that the polypeptides or protein antigens are bonded onto the musical immune substances. The polypeptides or the polypeptides or protein antigens are mixed with the musical immune substances at a ratio of 1-100:1-100, then magnetically stirred for 1 min to 10 min, stood for 0.5 h to 2 h at the room temperature, and ultra-centrifuged for 1 h to 3 h in a glycerol matrix at 20000 rcf (4° C.).

The musical immune substances in the solution 1/solution 2 need to be verified by various assays.

In a second aspect, the present invention provides an application of the mucosal immune preparation in preparing anti-tumor drugs.

The tumor includes but is not limited to submandibular gland carcinoma, lung adenocarcinomas or breast carcinoma, and metastatic carcinoma thereof.

The present invention further provides an application of the mucosal immune preparation in preparing anti-inflection drugs.

The infection includes but is not limited to viral infection, bacterial infection and parasitic infection.

The mucosal immune preparation of the present invention may be applied in human beings or other animals.

The mucosal immune preparation provided by the present invention may be administrated to a host alone, or administrated to a host in form of an inhalation preparation, an instillation preparation, a digestive duct preparation, a urogenital tract preparation or an external preparation prepared together with tumor-specific antigens or tumor-associated antigens (including tumor whole-cell antigens, tumor vesicles, and dendritic cells-carried antigens) and other vaccine antigen polypeptides (including viral vaccines, bacterial vaccines and parasitic vaccines) in a mucosal immunity manner. Particularly, the intranasal administration has the best therapeutic effect.

The mucosal immune preparation of the present invention acts on the body in form of an inhalation preparation, an instillation preparation, a digestive duct preparation, a urogenital tract preparation, an eye preparation or an external preparation in a mucosal immunity manner, and directly generates an immune reaction at a local part, so that the degradation of blood ribonucleases and the protein adhesion are prevented, and high compliance and small side effects are realized. Moreover, the mucosal immune preparation not only directly works at a local part but also can deliver these antibiotic substances to the whole body through passages such as thoracic ducts, so that the purposes of anti-infection and anti-tumor prevention and treatment are realized.

For the mucosal immune preparation of the present invention, in mice experiments, the effect of the intranasal administration is obviously superior to that of the subcutaneous injection.

For the mucosal immune preparation of the present invention, in volunteers with tumors, the safety of the intranasal administration is obviously superior to that of the subcutaneous injection.

After the mucosal immune preparation of the present invention is administrated alone by the nasal mucosa, there are no side effects on volunteers with advanced tumors, the life quality of the patients is improved, and the survival of the patients is prolonged. Therefore, it is proved that the mucosal immune preparation is both safe and effective.

After the mucosal immune preparation of the present invention is used together with chemotherapy, the side effects on volunteers with advanced tumors caused by the chemotherapy can be reduced obviously, the life quality of the patients is improved, and the survival of the patients is prolonged. Therefore, it is proved that the mucosal immune preparation is both safe and effective.

The mucosal immune preparation of the present invention can over-express inflammatory cytokines through immune cells and change the microenvironment of tumor cells, so as to attack the tumor cells by the immune cells and accelerate the tumor cell apoptosis; the mucosal immune preparation can eliminate or reverse the immunosuppression effect of Treg cells, so as to attack the tumor cells by the immune cells and accelerate the tumor cell apoptosis; the mucosal immune preparation can be bonded with receptors of TLR3, TLR4, RIG-I or MDA5 expressed by the tumor cells and thus directly trigger the tumor cell apoptosis, and there are no anticancer drugs based on the above targets at present; the mucosal immune preparation can be bonded with TLR3 for "invaded" target organ cells and compete with tumor exosome RNAs for being bonded with the TLR3 for "invaded" target organ cells, so as to block the formation of the tumor metastasis mechanism and prevent the tumor metastasis, and there are no anticancer drugs for preventing tumor metastasis based on the above targets at present; the mucosal immune preparation can also be bonded with TLR3 for "invaded" target organ cells and compete with tumor exosome RNAs for being bonded with the TLR4 for "invaded" target organ cells, so as to block the formation of the tumor metastasis mechanism and prevent the tumor metastasis, and there are no anticancer drugs for preventing tumor metastasis based on the above targets at present; the mucosal immune preparation can also be bonded with RIG-I for "invaded" target organ cells and compete with tumor exosome RNAs for being bonded with the RIG-I for "invaded" target organ cells, so as to block the formation of the tumor metastasis mechanism and prevent the tumor metastasis, and there are no anticancer drugs for preventing tumor metastasis based on the above targets at present; and, the mucosal immune preparation can also be bonded with MDA-5 for "invaded" target organ cells and compete with tumor exosome RNAs for being bonded with the MDA-5 for "invaded" target organ cells, so as to block the formation of the tumor metastasis mechanism and prevent the tumor metastasis, and there are no anticancer drugs for preventing tumor metastasis based on the above targets at present.

The raw materials or reagents involved in the present invention are ordinary commercially-available products or self-manufactured products; and, the involved operations are normal operations in the art, unless otherwise specified.

Based on the common knowledge in the art, the above preferred conditions can be combined with each other to obtain specific implementations.

The present invention has the following beneficial effects.

The present invention provides mucosal immune substances prepared from polyinosinic-polycytidylic acid, non-antibiotic amino compounds and at least one metal cation ($Ca^{2+}$, $Mg^{2+}$, $Zn^{2+}$, iron ion, lithium ion, etc.). When used with PEG, the mucosal immune substances can provide a slow release effect on a local part or the whole body, prolong the half-life period of the mucosal immune preparation, increase the effectiveness of drugs, and improve the compliance of patients.

The mucosal immune preparation provided by the present invention facilitates the mucosal immunity of the body by mucosal immunity and thus facilitate the activation and proliferation of various immune cells, including systemic nonspecific immunity, humoral immunity and cellular immunity, rather than merely acting on diseased local parts, so that a new idea of realizing the purposes of anti-infection and anti-tumor prevention and treatment is provided. Particularly, the realization of this new idea by the mucosal immunity will provide an opportunity to solve these challenges.

The mucosal immune preparation of the present invention has already been successfully tested in animal experiments and the volunteers with advanced tumors by mucosal immunity. After used in the animal experiments and the volunteers with cancers, the mucosal immune preparation of the present invention can cause local immunity and can reach target organs by blood through the antibiotic substances generated by the local immunity so as to realize the purposes of anti-tumor metastasis and anti-inflection in the whole body.

The mucosal immune preparation (spray or aerosol) provided by the present invention is used alone, or used with vaccines by nasal drip to simulate the respiratory mucosal immunity induced by natural infections so as to stimulate the body to generate systemic and mucosal local immune responses and induce the systemic immunity. Therefore, the mucosal immune preparation has better cross-immunity protection effect and has the advantages of high safety, easy vaccination, high patient compliance and the like.

Additionally, the mucosal immune preparation (spray or aerosol) provided by the present invention can be used for anti-inflection and anti-tumor prevention and treatment by the mucosal immunity through the digestive tract. The spray or aerosol of the present invention is used alone, or used with vaccines, then taken in and delivered to Peyer patches by M-cells, and processed and presented to T-lymphocytes by antigen-presenting cells, and lymphoid follicles are activated to generate sensitized T-lymphocytes and B-lymphocytes and memory T-lymphocytes and B-lymphocytes. The sensitized T-lymphocytes and B-lymphocytes enter the blood through mesenteric lymphatic aggregate nodules. A large amount of the sensitized T-lymphocytes and B-lymphocytes are brought to lamina propria through the blood circulation, and a small amount of the sensitized T-lymphocytes and B-lymphocytes enter other exocrine tissues. There are majority of ingredients of the immune system in the lamina propria, that is, there are a large amount of B-lymphocytes, plasmocytes, macrophagocytes, dendritic cells and T-lymphocytes. 15% of cells among enterocytes are lymphocytes, and 90% of lymphocytes are T-lymphocytes, so that the purposes of anti-infection and anti-tumor prevention and treatment are realized by facilitating the non-specific immunity and specific immunity.

The mucosal immune preparation (spray or aerosol) provided by the present invention can also be used for anti-inflection and anti-tumor prevention and treatment by the mucosal immunity through the urogenital tract, conjunctiva or an external preparation.

DETAILED DESCRIPTION OF THE INVENTION

The preferred implementations of the present invention will be described below in detail by embodiments. It should be understood that the following embodiments are merely for illustrative purpose and not intended to limit the scope of the present invention. Without departing from the purpose and spirit of the present invention, those skilled in the art can make various modifications and replacements to the present invention.

Unless otherwise specified, the experimental methods used in the following embodiments are conventional methods.

Unless otherwise specified, the materials, reagents and the like used in the following embodiments are commercially available.

Embodiment 1 Mucosal Immune Preparation and Preparation Method Thereof (1) A polyinosinic acid solution and a polycytidylic acid solution were prepared from polyinosinic acid and polycytidylic acid as raw materials by a PBS buffer solution, and the polyinosinic acid solution and the polycytidylic acid solution were stirred at 30° C. to 60° C. to obtain 0.5 mg/mL to 10 mg/mL of a double-stranded polyinosinic-polycytidylic acid solution (PIC solution).

(2) A chitosan oligosaccharide solution (COS solution) having a concentration of 1.6 mg/mL to 12.8 mg/mL was prepared from chitosan oligosaccharide by the PBS buffer solution.

(3) The COS solution was added dropwise in the double-stranded polyinosinic-polycytidylic acid solution obtained in the step (1) while stirring, a PEI solution was then added dropwise while stirring, and a $CaCl_2$) solution was added dropwise while stirring, to obtain a mucosal immune substance sample solution.

(4) The prepared mucosal immune substance sample solution was sterilized, filtered, and packaged in a proper spray bottle or aerosol bottle to obtain the product.

Embodiment 2 Mucosal Immune Preparation and Preparation Method Thereof (1) A polyinosinic acid solution and a polycytidylic acid solution were prepared from polyinosinic acid and polycytidylic acid as raw materials by a PBS buffer solution, and the polyinosinic acid solution and the polycytidylic acid solution were stirred at 30° C. to 60° C. to obtain 0.5 mg/mL to 10 mg/mL of a double-stranded polyinosinic-polycytidylic acid solution (PIC solution).

(2) A chitosan oligosaccharide solution (COS solution) having a concentration of 1.6 mg/mL to 12.8 mg/mL was prepared from chitosan oligosaccharide by the PBS buffer solution.

Or, a PEG-g-COS solution having a concentration of 1.6 mg/mL to 51.2 mg/mL was prepared from PEG-g-COS by the PBS buffer solution.

(3) The PEG-g-COS solution or the chitosan oligosaccharide solution was added dropwise in the double-stranded polyinosinic-polycytidylic acid solution obtained in the step (1) while stirring, and a $CaCl_2$) solution was then added dropwise while stirring to obtain a PIC-PEG-g-COS-$CaCl_2$) or PIC-COS-$CaCl_2$) compound.

(4) The PIC-PEG-g-COS-$CaCl_2$) or PIC-COS-$CaCl_2$) compound was stirred at a constant speed in a thermostatic magnetic stirrer and then added dropwise with 0.4 mg/mL to 6.0 mg/mL of an aqueous solution of sodium tripolyphosphate until obvious opalescence was observed, the reaction was maintained for 10 min to 60 min to obtain a mucosal immune substance through ionic crosslinking and self-assembly, and the mucosal immune substance was centrifuged at a high speed to obtain a mucosal immune substance having a particle size of less than 1000 nm.

(5) The prepared mucosal immune substance was re-suspended by distilled water, sterilized, filtered, and packaged in a proper spray bottle or aerosol bottle to obtain the product.

Experimental Example 1 Separate Application of Naristillae Mucosal Immune Preparation in Anti-Influenza Mice Protection Experiments Influenza virus: FM1 strain, purchased from the Institute of Virus Disease Control of Chinese Academy of Preventive Medicine.

Virazole: positive control drug, purchased from Shenyang Yanfeng Pharmacy Factory.

Mice: Kunming species, where mice 8 g to 10 g were used for passage of FM1 virus, and mice 14 g to 20 g were used for the following normal experiments.

The influenza virus FM1 strain suspension could lead to fetal pneumonia of mice at a ratio of 5 $LD_{50}$/mouse by nasal drip. The mice were infected first and administrated with drugs during the experiment, and then grouped in accordance with Table 1.

TABLE 1

Application of the mucosal immune preparation of the present invention in anti-influenza mice protection experiments by nasal drip

| Group | Administration dosage | Death rate % | $X^2$ | P value |
|---|---|---|---|---|
| Influenza virus FM1 strain | Normal saline | 89 | | |
| Positive control virazole | 0.07 g/kg/d | 63 | 1.64 | >0.05 |
| Separate naristillae of the present invention | 0.1 ml/mouse | 43 | 3.88 | <0.05 |

The experimental results had shown that, in the mice protection experiments, the non-specific anti-influenza effect of the separate naristillae mucosal immune preparation of the present invention was superior to that of the known antiviral drug virazole, and had remarkable anti-influenza virus effects by statistical analysis.

Experimental Example 2

This experimental example was used for describing the comparison of the influences of the mucosal immune preparation (naristillae) of the present invention in combination with the nasal mucosal immunity and subcutaneous injection immunity of an influenza vaccine and the complete Freund's adjuvant on the titer of the humoral antibody IgA and the influenza virus proliferation.

The experimental scheme was as follows.

Influenza virus: FM1, purchased from the Institute of Virus Disease Control of Chinese Academy of Preventive Medicine.

Influenza vaccine: split influenza vaccine produced by Hualan Biological Product Co., Ltd.

Complete Freund's adjuvant: produced by Shanghai Wegene Biotechnology Co., Ltd.

Mucosal immune adjuvant of the present invention: produced by Xinfu (Beijing) Pharmaceutical Technology Co., Ltd.

Mice: Kunming species, where mice 8 g to 10 g were used for passage of FM1 virus, and mice 14 g to 20 were used for the following normal experiments.

Complete Freund's adjuvant influenza vaccine: in a centrifuge tube, the vaccine and the complete Freund's adjuvant at the same volume were uniformly mixed by vortex to obtain water-in-oil emulsion.

Naristillae of the combined influenza vaccine of the present invention: the influenza vaccine and the mucosal immune adjuvant of the present invention were mixed at the same volume to obtain an aqueous solvent.

Influenza vaccine: the influenza vaccine and PBS were mixed at the same volume to obtain an aqueous solvent.

Immunization Method:

Subcutaneous injection immunization: immune mice were injected subcutaneously for 0 day and injected for 28 days at a ratio of 0.1 ml/mouse; on the $42^{rd}$ day, blood was drawn from some mice, the serum was separated, and the titer of the antibody was measured; other mice were infected with the influenza virus FM1 strain suspension at a ratio of 5 $LD_{50}$/nasal drop, and the titer of the lung tissue virus was measured on the fifth day after the inflection.

Nasal immunization: immune mice were injected subcutaneously for 0 day and injected for 28 days at a ratio of 0.1 ml/mouse; on the $42^{rd}$ day, blood was drawn from some mice, the serum was separated, and the titer of the antibody was measured; other mice were infected by the influenza virus FM1 strain suspension at a ratio of 5 $LD_{50}$/nasal drop, and the titer of the lung tissue virus was measured on the fifth day after the inflection.

The experimental results of the groups were shown in Table 2:

TABLE 2

Anti-influenza experiments of the mucosal immune preparation of the present invention in combination with the influenza vaccine by nasal drip

| Group | Antibody index | Titer of influenza virus after treatment |
|---|---|---|
| Subcutaneous injection immunization: | | |
| Influenza vaccine | $10^{3.1}$ | $10^4$ |
| Complete Freund's adjuvant influenza vaccine | $10^{5.5}$ | $10^{3.5}$ |
| Naristillae of the combined influenza vaccine of the present invention | $10^{4.5}$ | $10^{2.0}$ |
| Nasal mucosal immunization: | | |
| Influenza vaccine | $10^{2.5}$ | $10^{4.5}$ |
| Naristillae of the combined influenza vaccine of the present invention | $10^4$ | <10 |
| FM1 virus control | $10^{5.0}$ | |

The complete Freund's adjuvant was a golden standard for detecting the cellular immunity of the body. The experimental results had indicated that, in the subcutaneous immunization, the titer of the antibody generated by the combined influenza vaccine of the mucosal immune preparation of the present invention was lower 10 times than that of the complete Freund's adjuvant influenza vaccine, but the titer of influenza virus was reduced by 31.6 times in comparison to the complete Freund's adjuvant influenza vaccine. Particularly, the nasal mucosal immunization of mice had indicated that the tiger of the antibody generated by the naristillae obtained by combining the mucosal immune preparation of the present invention with the antigen was higher 31.6 times than that of the pure influenza vaccine, and the titer of influenza virus was reduced by above 3100 times, so that the mucosal immune preparation had obvious effects.

Experimental Example 3

It was detected by Beijing Jingmeng High-tech Stem Cell Technology Co., Ltd. that the present invention had significant effects in the preliminary detection of CIK cell effector target tests.

Sample No.: JSCIK2016042614; detection date: 2016.04.26; and, report date: 2016.04.28.

Operation procedure: culturing and analyzing in accordance with the CIK cell effector target test SOP.

Target cell: A549; effector cell: cultured JSCIK2016042614.

Conclusion: by a fluorescence microscope and an ELIASA detection method and the experimental error, the killing capability of the cells JSCIK2016042614 was comprehensively analyzed, which was moderate with a ratio of 1:10.

Experimental Example 4

The results of salvage therapy of four volunteers with end-stage or advanced tumors by the mucosal immune preparation of the present invention will be described below.

1. Usage: the anti-tumor drug of the present invention is a non-cytotoxic drug. The drug was administered nasally every other day at a volume of 2 mg to 6 mg and administrated for 1 to 12 months, without other obvious side effects.

2. Clinical effects: referring to Table 3.

Table 3 Application of the mucosal immune preparation of the present invention in volunteers with end-stage or advanced tumors by nasal immunization

| Name | Gender | Age | Disease | Before administration | After administration | Time of duration |
|---|---|---|---|---|---|---|
| LIN Shulan | Female | 80 years old | Carcinoma of submandibular gland, multiple metastatic sites, recurrence after surgery twice, multiple organ metastasis. The doctor thought she only had 2 months lifetime in May 2016. | Lie in bed, low appetite, accompanied by nausea and emesis, only one meal a day, spirit drooping. Need to actively support treatment with blood and protein. | Appetite increased since October, 3 meals a day, put on weight, good mental state, lifetime has prolong 11 months (from July 2016 to June 2017) than doctor's prediction. Since local pain and induration were found in injected part, the drug was then administrated by nasal administration. The good state has kept to the present, and the patient has already been discharged from the hospital. | From June 2016 to June 2017 |
| WEN Qingqiang | Male | 67 years old | Lung adenocarcinoma; he was diagnosed with lung cancer in Peking Union Hospital and Tianjin Quanjian Hospital on February and March 2017; there was a duck-egg-sized tumor in the mediastinum. | Spirit drooping, no surgery, chemotherapy. | The drug is administrated nasally at a volume of 6 mg/each time and administrated every other day, without side effects. The side effects were reduced by the mucosal immune preparation in combination with the chemotherapeutic drug (cisplatin), almost no nausea and emesis occurred, and the number of leucocytes was increased from 1000/mm$^3$ to 2000/mm$^3$ before administration to 3000/mm$^3$ after administration. | From March 2017 to June 2017 |
| ZHU Shuqin | Female | 62 years old | She was diagnosed with right breast cancer and metastasis in liver on May 8, 2017 in Jilin Tumor Hospital, and cancer nests in fiber texture were found in lymph nodes. | Severe side effects after wo chemotherapies, weight loss, nausea and emesis, and increased tumor. High content of transaminase. | Since May 4, 2017, the drug was administrated nasally every other day at a volume of 4 mg/each time, then injected intramuscularly at a volume of 2 mg/each time. In such administration circulation, after more than ten times of administration, the patient said that there were no side effects. In combination with the chemotherapeutic drug, the side effects of the chemotherapy were significantly reduced, the appetite was increased, the physical strength was increased, and the breast tumor was softened. The content of glutamic-pyruvic transaminase was decreased from 130.5 U/L to 38.4 U/L. The maximum low-echo halo of the liver was decreased from 7.6 × 5.1 cm to 5.9 × 3.0 cm on Apr. 8, 2017 to 5.9 × 3.0 cm on Jun. 2, 2017. | From May 2017 to June 2017 |

-continued

| Name | Gender | Age | Disease | Before administration | After administration | Time of duration |
|---|---|---|---|---|---|---|
| WANG Xiufang | Female | 73 years old | Coloretal cancer surgery in 2002, breast cancer surgery in 2008, lung cancer surgery in 2015, and lung cancer radiotherapy and chemotherapy in April 2017. | No appetite, no taste, light sleep, tired and weak, mild hair loss, poor gastric kinetic energy, cough and take cough medicines, and no treatment. | Since May 27, 2017, the drug was administered nasally every other day at a volume of 4 mg/each time. After six times of drug administration, the patient and her family members said that there were no side effects. The appetite was increased, the tumor was decreased, the cough was relieved greatly, and the cough medicines were not administrated. | From May 2017 to June 2017 |

3. It can be known from the above results that the mucosal immune preparation of the present invention has the following advantages: (1) good safety; (2) the mucosal immune preparation can reduce the side effects of the chemotherapy; (3) the clinical effects are significant: the appetite is increased, the physical strength is increased, and the mental state becomes optimistic from pessimistic and becomes confident, and the total survival time is prolonged at least several months in comparison to the survival time predicted by the chief physician; and (4) the applications in the volunteers with advanced tumors have proved that the mucosal immune preparation can obviously reduce the side effects resulted from the chemotherapy, significantly improve the life quality of the patients and prolong the survival time of the patients, so that the mucosal immune preparation is both safe and effective.

4. It can be known from ZHU Shuqin's case that the product not only has an anticancer effect on a local part by nasal spray, but also can have a systemic immunity effect after the nasal mucosal immunization and have astonishing effects on metastatic cancers.

5. Selection of tested populations of the present invention: in accordance with Technical Guidelines for Clinical Trials of Anti-cancer Drugs issued by the State Food and Drug Administration, the score for the performance status (PS) ECOG of the selected cancer patients is 0 to 1 or the score for Karnofsky of the patients is higher than 70 scores, referring to Table 1 and Table 5.

TABLE 4

Scoring standard for ECOG performance status

| Score | Activity level |
|---|---|
| 0 | Completely normal, being able to do all normal activities without any restriction |
| 1 | Being unable to do vigorous physical activities, but being able to move around and do light physical activities or office work |
| 2 | Being able to move around and take care of themselves in daily life, but being unable to do any job, the time in bed in the daytime being not more than 50% |
| 3 | Being able to barely take care of themselves in daily life, the time in bed or on a chair for rest in the daytime being more than 50% |
| 4 | Completely incapacitated, being unable to take care of themselves in daily life, being in bed or using a wheelchair |
| 5 | Dead |

TABLE 5

Scoring standard for Karnofsky performance status

| Score | Activity level |
|---|---|
| 100 | Being able to do normal activities, no complaints or disease symptoms |
| 90 | Being able to do normal activities, with slight disease symptoms |
| 80 | Being able to barely do normal activities, with some symptoms or signs |
| 70 | Being able to take care of themselves in daily life, but unable to maintain normal activities or positive work |
| 60 | Occasionally needing help from others, but being able to take care of themselves in daily life most of the time |
| 50 | Frequently needing help from others, or needing frequent medical care |
| 40 | Being unable to take care of themselves in daily life, and needing special help and care |
| 30 | Being completely unable to take care of themselves in daily life, should be in the hospital, without death risk |
| 20 | Must be in the hospital, in serious condition, positively supporting the treatment |
| 10 | Being terminally ill, impending death |
| 0 | Dead |

The selection of treatment objects in the present invention is performed after patients have known ineffective cancer treatment or abandon the treatment and have signed the Informed Consent. The performance requirement is far lower than the above standards. Majority of patients have an ECOG in the fifth level or a Karnofsky score of greater than 20 scores. That is, patents who lose the self-care ability, are in a bad condition and need to positively support treatment are possible, without any age limit. The present invention has certain effects on the all patients.

Experimental Example 5

This experimental example was used for describing the following situations: precipitation will be generated by increasing the dosage of COS in the mucosal immune preparation of the present invention so that the uniformity of drug administration is affected; after the addition of PEI, the precipitation will be prevented; and, by increasing the dosage of COS, the mucosal immunity is further enhanced (referring to Table 6).

TABLE 6

| Name | PIC (mg/ml) | COS (mg/ml) | PEI (mg/ml) | CaCl$_2$ (mol/L) | Result |
|---|---|---|---|---|---|
| Group 1 | 1 | 0.4 | 0 | 0.0004 | Clear solution |
|  | 1 | 0.8 | 0 | 0.0004 | Clear solution |
|  | 1 | 1.6 | 0 | 0.0004 | Precipitation |
| Group 2 | 1 | 0.8 | 32 | 0.0004 | Clear solution |
|  | 1 | 1.6 | 32 | 0.0004 | Clear solution |
|  | 1 | 3.2 | 32 | 0.0004 | Clear solution |
|  | 1 | 6.4 | 32 | 0.0004 | Clear solution |

Comparison Example 1

Patent Application No. CN105396130A disclosed "a polyinosinic-polycytidylic acid, ammonia and calcium adjuvant and a vaccine containing the PIC, ammonia and calcium adjuvant", and disclosed that the non-antibiotic amino compound is optionally chitosan.

Chitosan oligosaccharide in Embodiment 1 is replaced with chitosan in this comparison example, and the result of comparison of the influences of the both on the uniformity of drug administration refers to Table 7.

It is found by researches that the addition of the chitosan solution leads to the generation of precipitation during the preparation process and thus influences the uniformity of drug administration; however, this problem can be solved by using chitosan oligosaccharide. (referring to Table 7).

TABLE 7

| Name | PIC (mg/ml) | CS (mg/ml) | COS (mg/ml) | CaCl$_2$ (mol/L) | Result |
|---|---|---|---|---|---|
| Group 1 | 1 | 0.4 | 0 | 0.0004 | Precipitation |
|  | 1 | 0.8 | 0 | 0.0004 | Precipitation |
| Group 2 | 1 | 0 | 0.4 | 0.0004 | Clear solution |
|  | 1 | 0 | 0.8 | 0.0004 | Clear solution |

Although the present invention has been described above in detail by general description and specific implementations, it is apparent for those skilled in the art to make some modifications or improvements based on the present invention. Therefore, those modifications or improvements made without departing from the spirit of the present invention shall fall into the protection scope of the present invention.

What is claimed is:

1. An immune preparation, comprising an immune substance formed by polyinosinic-polycytidylic acid, polyethylene glycol (PEG)-grafted chitosan oligosaccharide, and at least one metal ion, wherein the immune preparation is suitable for mucosal administration, and wherein the immune preparation does not contain an antibiotic, and chitosan oligosaccharide in the PEG-grafted chitosan oligosaccharide has a molecular weight of less than 3200 Da.

2. The immune preparation according to claim 1, wherein the immune preparation is a spray or an aerosol.

3. The immune preparation according to claim 2, wherein the immune preparation comprises a propellant.

4. The immune preparation according to claim 2, wherein the metal ion is Ca'.

5. The immune preparation according to claim 4, wherein the weight ratio of polyinosinic-polycytidylic acid to PEG-grafted chitosan oligosaccharide is from 0.01 to 6.25.

6. The immune preparation according to claim 4, wherein the immune substance has a particle size of less than 1000 nm.

7. The immune preparation according to claim 6, wherein the immune preparation further comprises at least one of antigens, chemical drugs and biological immune drugs.

8. A method for anti-infection of a subject having at least one of a viral infection, bacterial infection and parasitic infection, the method comprising:
    administering, via a mucosal administration route, the immune preparation of claim 1 to the subject in need thereof.

9. The method of claim 8, wherein the mucosal administration route is transnasal.

10. A method of treating a subject having a metastatic carcinoma, the method comprising:
    administering, via a mucosal administration route, the immune preparation of claim 1 to the subject in need thereof.

11. The method of claim 10, wherein the mucosal administration route is transnasal.

* * * * *